(12) United States Patent
Coney et al.

(10) Patent No.: US 11,105,323 B2
(45) Date of Patent: Aug. 31, 2021

(54) MOTOR DRIVE SYSTEM AND METHOD

(71) Applicant: Franklin Electric Co., Inc., Fort Wayne, IN (US)

(72) Inventors: Jason L. Coney, Fort Wayne, IN (US); Jared E. Evans, Fort Wayne, IN (US); Robert C. Smith, Ossian, IN (US)

(73) Assignee: FRANKLIN ELECTRIC CO., INC., Fort Wayne, IN (US)

( * ) Notice: Subject to any disclaimer, the term of this patent is extended or adjusted under 35 U.S.C. 154(b) by 363 days.

(21) Appl. No.: 16/343,383

(22) PCT Filed: Oct. 20, 2017

(86) PCT No.: PCT/US2017/057690
§ 371 (c)(1),
(2) Date: Apr. 18, 2019

(87) PCT Pub. No.: WO2018/075942
PCT Pub. Date: Apr. 26, 2018

(65) Prior Publication Data
US 2019/0277277 A1 Sep. 12, 2019

Related U.S. Application Data

(60) Provisional application No. 62/411,507, filed on Oct. 21, 2016, provisional application No. 62/411,505, filed on Oct. 21, 2016.

(51) Int. Cl.
*F04C 14/06* (2006.01)
*F04B 17/03* (2006.01)
(Continued)

(52) U.S. Cl.
CPC .............. *F04B 17/03* (2013.01); *A61M 5/14* (2013.01); *A61M 5/142* (2013.01); *F04B 47/02* (2013.01);
(Continued)

(58) Field of Classification Search
CPC .... F04C 2270/025; F04C 14/06; F04C 28/06; F04C 2/107–1078; F04C 13/008;
(Continued)

(56) References Cited

U.S. PATENT DOCUMENTS

| 4,162,437 A | * | 7/1979 | Keith | ................... H02P 27/02 |
| | | | | 388/854 |
| 5,841,260 A | * | 11/1998 | Imai | ................... G11B 19/04 |
| | | | | 318/638 |

(Continued)

FOREIGN PATENT DOCUMENTS

| RU | 2181829 | 4/2002 |
| RU | 2341004 | 12/2008 |

OTHER PUBLICATIONS

International Preliminary Report on Patentability received for PCT Patent Application No. PCT/US2017/057690, dated May 2, 2019, 8 pages.

(Continued)

*Primary Examiner* — Alexander B Comley
*Assistant Examiner* — Thomas Fink
(74) *Attorney, Agent, or Firm* — Faegre Drinker Biddle & Reath LLP

(57) ABSTRACT

A water pumping system, a motor drive, and a method of starting pumping by the motor drive. The method includes performing repeated starting attempts to overcome stiction in a progressive cavity pump by attempting to supply power to an electrical motor at increasing power levels in each starting attempt and supplying the power at the increasing power levels if the power is available in from a power source; and after each starting attempt: reducing the power applied to the electrical motor to a reduced power level; determining a rotational speed of the electrical motor; determining if the rotational speed matches a speed corresponding to the reduced power level applied to the electrical
(Continued)

motor; if the rotational speed does not match and a predetermined number of starting attempts has not been reached, performing a next starting attempt; and if the rotational speed does match, entering a normal mode of operation.

22 Claims, 6 Drawing Sheets

(51) Int. Cl.

| | | |
|---|---|---|
| *F04B 49/06* | (2006.01) | |
| *F04C 2/107* | (2006.01) | |
| *H02P 6/24* | (2006.01) | |
| *A61M 5/14* | (2006.01) | |
| *H02P 29/024* | (2016.01) | |
| *F04C 15/00* | (2006.01) | |
| *F04C 14/08* | (2006.01) | |
| *A61M 5/142* | (2006.01) | |
| *F04B 47/06* | (2006.01) | |
| *H02P 6/06* | (2006.01) | |
| *H02P 29/10* | (2016.01) | |
| *F04B 47/02* | (2006.01) | |
| *F04B 51/00* | (2006.01) | |
| *E21B 43/12* | (2006.01) | |

(52) U.S. Cl.
CPC .............. *F04B 47/06* (2013.01); *F04B 49/06* (2013.01); *F04B 49/065* (2013.01); *F04B 51/00* (2013.01); *F04C 2/1071* (2013.01); *F04C 14/06* (2013.01); *F04C 14/08* (2013.01); *F04C 15/008* (2013.01); *H02P 6/06* (2013.01); *H02P 6/24* (2013.01); *H02P 29/0241* (2016.02); *H02P 29/10* (2016.02); *E21B 43/128* (2013.01); *F04B 2203/0209* (2013.01); *F04C 2270/025* (2013.01)

(58) Field of Classification Search
CPC ........ F04B 49/02; H02P 1/00–02; H02P 1/04; H02P 7/00; H02P 8/14–165; F04D 13/068; F04D 25/0673
See application file for complete search history.

(56) References Cited

U.S. PATENT DOCUMENTS

| | | | |
|---|---|---|---|
| 6,041,856 A | 3/2000 | Thrasher | |
| 6,045,333 A | 4/2000 | Breit | |
| 6,468,058 B1 * | 10/2002 | Breit | F04C 13/008 417/423.3 |
| 7,042,180 B2 | 5/2006 | Terry et al. | |
| 7,358,694 B2 * | 4/2008 | Won | H02P 6/20 318/254.1 |
| 7,437,215 B2 | 10/2008 | Anderson | |
| 7,869,978 B2 | 1/2011 | Anderson | |
| 8,152,492 B2 | 4/2012 | Beck | |
| 10,001,121 B2 | 6/2018 | Van der Merwe | |
| 2004/0062658 A1 | 4/2004 | Beck | |
| 2006/0130481 A1 | 6/2006 | Browe | |
| 2007/0014056 A1 * | 1/2007 | Andersen | H02H 3/006 361/23 |
| 2007/0212229 A1 | 9/2007 | Stavale | |
| 2008/0066478 A1 * | 3/2008 | Okamoto | F25B 49/022 62/151 |
| 2008/0067116 A1 | 3/2008 | Anderson | |
| 2008/0240932 A1 | 10/2008 | Carstensen | |
| 2009/0096398 A1 * | 4/2009 | Kyrtsos | H02P 29/032 318/432 |
| 2009/0292245 A1 | 11/2009 | Basso et al. | |
| 2010/0034665 A1 | 2/2010 | Zhong | |
| 2011/0181431 A1 | 7/2011 | Koehl | |
| 2012/0003112 A1 | 1/2012 | Hayashimoto | |
| 2012/0087805 A1 | 4/2012 | Marioni | |
| 2012/0101788 A1 | 4/2012 | Kallesoe | |
| 2012/0177504 A1 | 7/2012 | Beck | |
| 2013/0151216 A1 | 6/2013 | Palka | |
| 2016/0115959 A1 | 4/2016 | Cheng | |
| 2019/0097549 A1 * | 3/2019 | Colby | H02P 1/022 |
| 2019/0249650 A1 | 8/2019 | Coney et al. | |
| 2019/0271303 A1 * | 9/2019 | Endo | F04B 17/03 |

OTHER PUBLICATIONS

International Search Report and Written Opinion received for PCT Patent Application No. PCT/US2017/057690, dated Jan. 4, 2018, 8 pages.

* cited by examiner

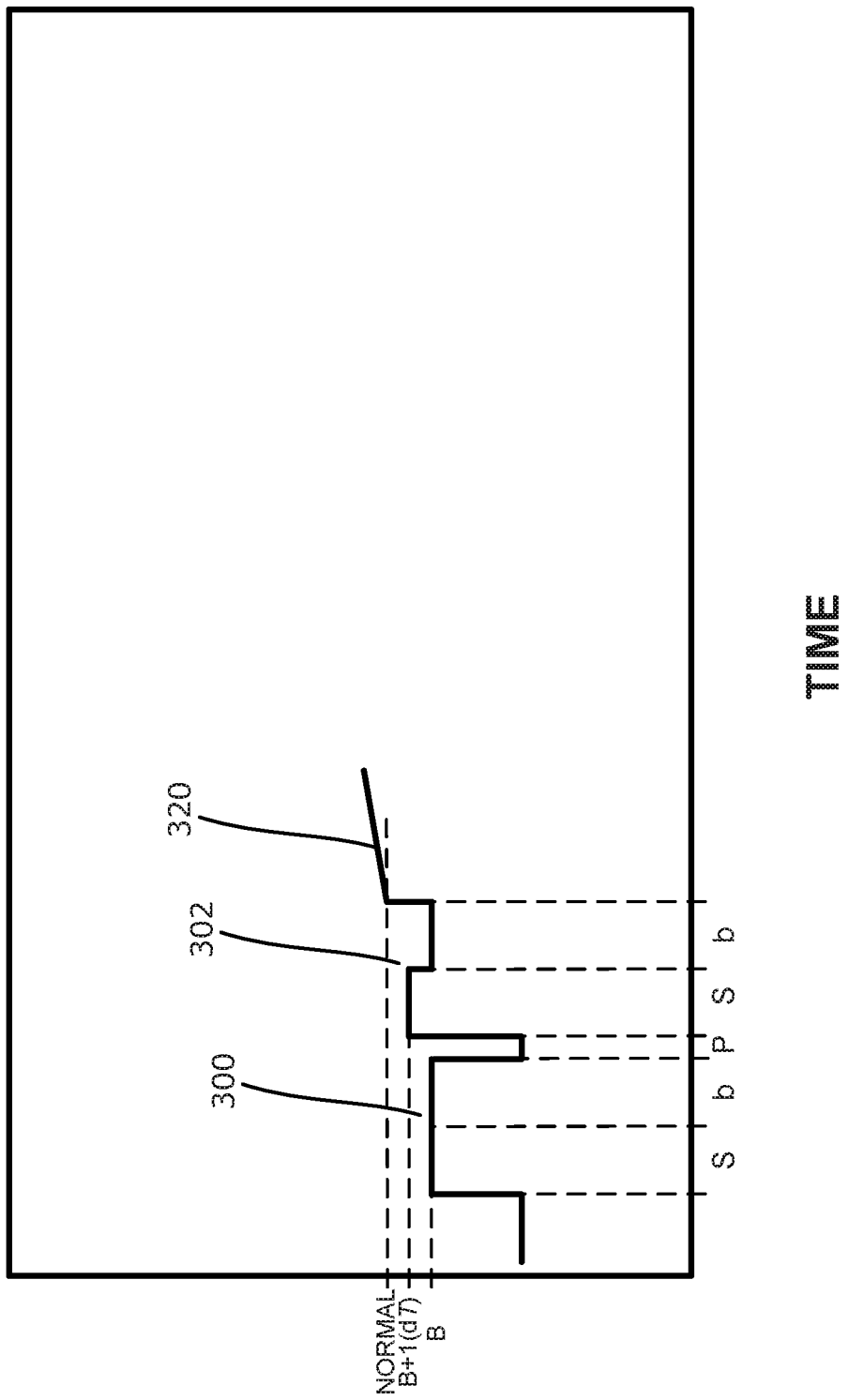

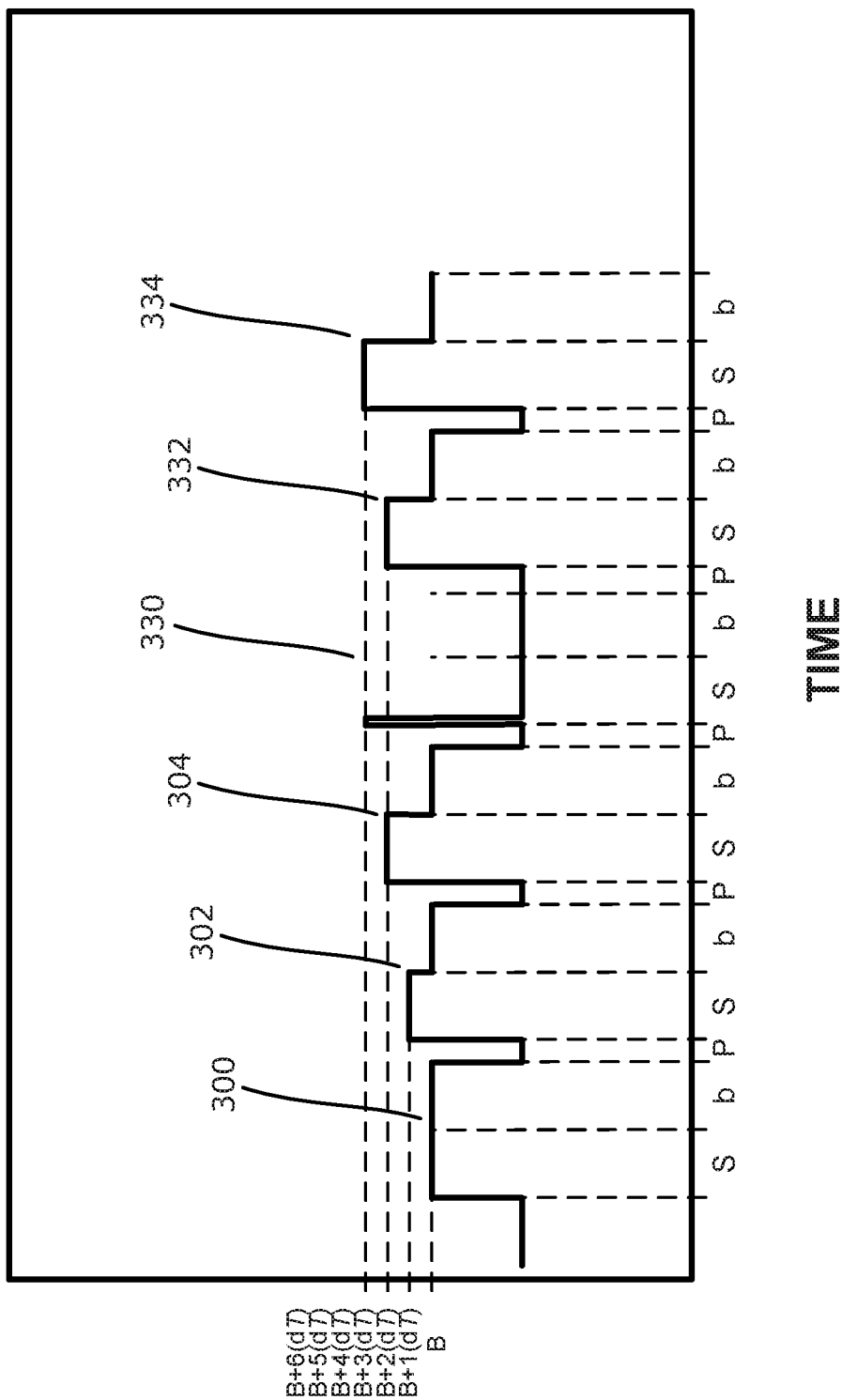

MOTOR DRIVE SYSTEM AND METHOD

CROSS-REFERENCE TO RELATED APPLICATIONS

The present application is a § 371 National Stage entry of International Application No. PCT/US2017/057690 titled MOTOR DRIVE SYSTEM AND METHOD, filed on Oct. 20, 2017, which claims the benefit of priority from U.S. Provisional Patent Applications Nos. 62/411,505 and 62/411,507, both filed Oct. 21, 2016, said applications incorporated by reference herein in their entirety.

FIELD OF THE DISCLOSURE

The disclosure relates generally to a system and a method for driving a motor. More particularly, the disclosure relates to a system and method for adaptively controlling an operating characteristic of the motor in a fluid pumping system.

BACKGROUND OF THE DISCLOSURE

Fluid pumping systems use motors to drive pumps and transfer fluids from supply reservoirs such as wells. A sensor measures a characteristic of the fluid, and a motor drive controls the motor to maintain the characteristic near its setpoint. In some systems, the motor drive measures pressure in a fluid circuit and controls the speed of the motor to maintain the pressure near its setpoint.

The pump must operate against the well head. Wells can be deep or shallow, and the fluid level within each well varies. The pump pressure can therefore be significantly higher than the pressure sensed by the pressure sensor. The pump pressure can vary significantly between installations and also within the same installation as the level of the fluid in the well rises or falls.

Pumping systems can be used in developed and developing countries to pump water, often in remote locations. In many applications it is desirable to provide a low cost system that is simple to use and does not require calibration or tuning by the user. Low cost and simple systems are typically more reliable as they have fewer complexities, which further enhances their value.

Helical rotor pumps have a high starting friction, or stiction. If stiction is not overcome, the pump may stall indefinitely, particularly if the power source of the motor drive driving the pump is at times constrained, such as a renewable energy power source. Improve methods for starting helical rotor pumps are desired.

SUMMARY

Embodiments of a water pumping system, a motor drive, and a method of starting pumping by the motor drive are disclosed. In some embodiments, the method comprises: performing repeated starting attempts to overcome stiction in a progressive cavity pump by attempting to supply power to an electrical motor driving the progressive cavity pump at increasing power levels in each starting attempt and supplying the power at the increasing power levels if the power is available from a power source; and after each starting attempt: reducing the power applied to the electrical motor to a reduced power level; determining a rotational speed of the electrical motor at the reduced power level; determining if the rotational speed matches a speed corresponding to the reduced power level applied to the electrical motor; if the rotational speed does not match the speed corresponding to the reduced power level, and a predetermined number of starting attempts has not been reached, performing a next starting attempt; and if the rotational speed does match the speed corresponding to the reduced power level, entering a normal mode of operation.

In some embodiments, a motor drive is configured to start a progressive cavity pump in a water pumping system, and comprises a controller including control logic configured to perform the method comprising: performing repeated starting attempts to overcome stiction in the progressive cavity pump by attempting to supply power to an electrical motor driving the progressive cavity pump at increasing power levels in each starting attempt and supplying the power at the increasing power levels if the power is available from a power source; and after each starting attempt: reducing the power applied to the electrical motor to a reduced power level; determining a rotational speed of the electrical motor at the reduced power level; determining if the rotational speed matches a speed corresponding to the reduced power level applied to the electrical motor; if the rotational speed does not match the speed corresponding to the reduced power level, and a predetermined number of starting attempts has not been reached, performing a next starting attempt; and if the rotational speed does match the speed corresponding to the reduced power level, entering a normal mode of operation.

In some embodiments, a water pumping system comprises a progressive cavity pump; an electrical motor coupled to the progressive cavity pump; and a motor drive to power the electrical motor, the electrical motor drive configured to start the progressive cavity pump and to drive the progressive cavity pump in a normal mode of operation after starting the progressive cavity pump, the motor drive including a controller comprising control logic configured to perform the method comprising: performing repeated starting attempts to overcome stiction in the progressive cavity pump by attempting to supply power to an electrical motor driving the progressive cavity pump at increasing power levels in each starting attempt and supplying the power at the increasing power levels if the power is available from a power source; and after each starting attempt: reducing the power applied to the electrical motor to a reduced power level; determining a rotational speed of the electrical motor at the reduced power level; determining if the rotational speed matches a speed corresponding to the reduced power level applied to the electrical motor; if the rotational speed does not match the speed corresponding to the reduced power level, and a predetermined number of starting attempts has not been reached, performing a next starting attempt; and if the rotational speed does match the speed corresponding to the reduced power level, entering a normal mode of operation.

DESCRIPTION OF THE DRAWINGS

The features and advantages of the disclosure will become more readily appreciated as the same become better understood by reference to the following detailed description when taken in conjunction with the accompanying drawings, where:

FIGS. 4 to 6 are timing diagrams provided to illustrate the functionality of control logic embodied in the method described with reference to FIG. 3.

Figure 1:
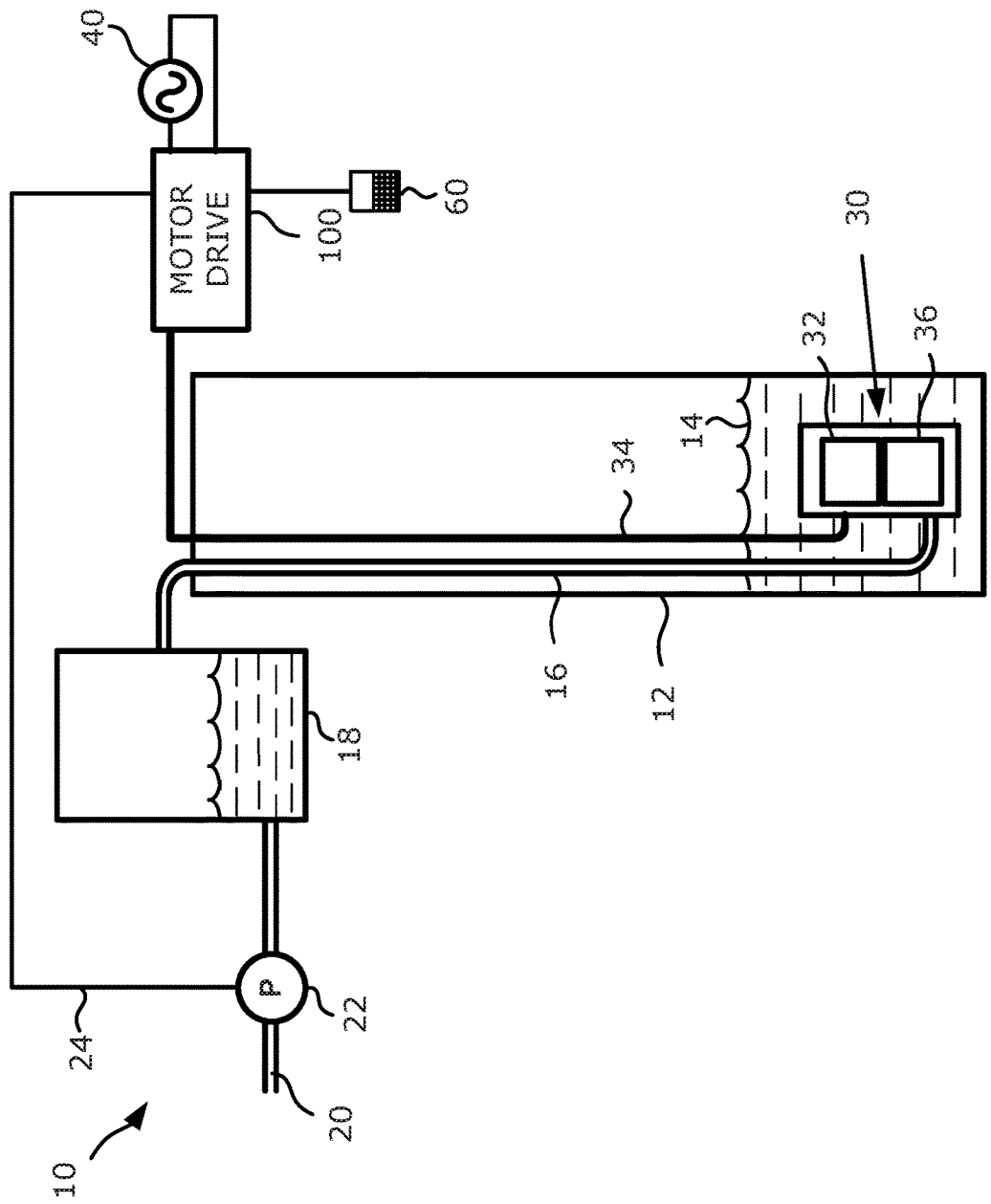
FIG. 1 is a diagrammatic representation of an embodiment of a liquid supply system.

Corresponding reference characters indicate corresponding parts throughout the several views. Although the drawings represent embodiments of various features and components according to the present invention, the drawings are not necessarily to scale and certain features may be exaggerated in order to better illustrate and explain the present invention.

DETAILED DESCRIPTION OF DISCLOSED EMBODIMENTS

For the purpose of promoting an understanding of the principles of the invention, reference will now be made to the embodiments illustrated in the drawings, which are described below. The embodiments disclosed below are not intended to be exhaustive or limit the invention to the precise form disclosed in the following detailed description. Rather, the embodiments are chosen and described so that others skilled in the art may utilize their teachings. It will be understood that no limitation of the scope of the invention is thereby intended.

Except where a contrary intent is expressly stated, terms are used in their singular form for clarity and are intended to include their plural form.

As used herein, the terms "comprising," "containing," "having" and "including" denote an open transition meaning that the claim in which the open transition is used is not limited to the elements following the terms "comprising" or "including". By contrast, the terms "consisting of" or "consists of" denote closed transitions.

Occurrences of the phrase "in one embodiment," or "in one aspect," herein do not necessarily all refer to the same embodiment or aspect.

Helical rotor pumps are well known for high stiction and when used from a constrained power source, such as a photovoltaic (PV) panel array, the power needed to start the pump can easily exceed the available power, resulting in a stalled condition. A starting method is provided herein that will start a helical rotor pump without exceeding the power available from a constrained power source while also preventing the stalled condition. Additionally, if the power source is unconstrained, the starting method will start the helical rotor pump utilizing the lowest starting torque level, thereby conserving energy. A helical rotor pump is a type of progressive cavity pump. Progressive cavity pumps also include centrifugal pumps. Progressive cavity pump and helical rotor pump are used interchangeably herein. Progressive cavity pumps are also known as cavity pumps and eccentric screw pumps.

The foregoing exemplary embodiments of the disclosure will now be described with reference to the figures. Referring to FIG. 1, a diagrammatic representation of a liquid supply system 10 is disclosed. Example liquids include water, gasoline fuel, diesel fuel, petroleum, oil, sewage, and combinations of such liquids with gases and solids, such as water and coal-based methane gas. Although the embodiments below may be described with reference to water, the invention is not so limited and the principles and advantages thereof may be applicable to any liquid. The liquid supply system comprises a reservoir 12 containing water 14 which is pumped by a pump unit 30 through a conduit 16, optionally via a reservoir 18, e.g. a pressure tank, to a conduit 20 of a closed system. Pump unit 30 includes a pump 36 driven by a motor 32 which is powered by a motor drive 100 via power conductors 34. The size of reservoir 12, which is interposed between pump unit 30 and a pressure sensor, affects the response of the system. In one example, motor drive 100 is a variable frequency drive (VFD) and pump 36 is a helical rotor pump. Power conductors 34 may comprise two or more wires to provide single or three phase power to motor 32.

During operation of the system, water 14 flows out of conduit 20. For example, the system may be a water system in a home, in which case water flows out of conduit 20 when a faucet is opened or an irrigation system is turned on. Constant pressure ensures the heads of the irrigation system spray at a constant distance from the head to provide even and predictable irrigation. Fluid characteristics including pressure may be monitored with a pressure sensor 22 disposed in conduit 20 to generate a pressure signal useful to maintain pressure about a setpoint. The pressure signal is provided via line 24 connecting pressure sensor 22 and motor drive 100. An exemplary input device 60 is also shown. Input device 60 is provided to receive, from a user, input parameters such as setpoints and schedules. Input device 60 may comprise a smart device wirelessly coupled to motor drive 100. Example smart devices include computers, smart phones and tablets. Reservoir 12 may be an aboveground or underground tank, a well casing, or any other reservoir containing water 14.

Figure 2:
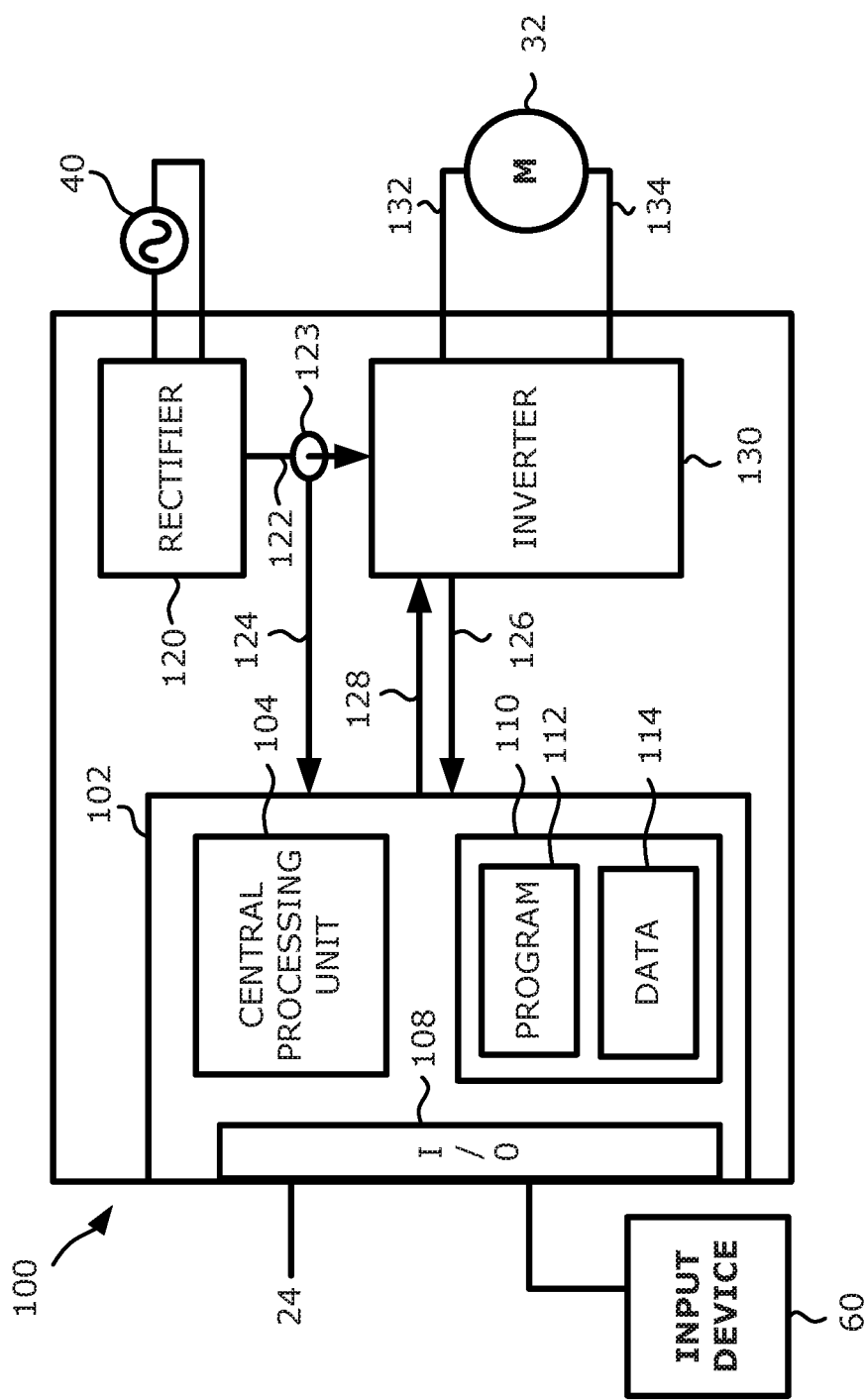
FIG. 2 is a block diagram of an embodiment of a motor drive.

FIG. 2 illustrates an embodiment of motor drive 100 comprising a processing device, illustratively controller 102, a rectifier 120 and an inverter 130. As shown, controller 102 includes a CPU 104 configured to access a memory device 110 and execute processing instructions from a software application, exemplified by program 112, based on data 114. Techniques for generating motor voltages according to characteristics of a control signal are known in the art. In one example, a technique comprises storing values in a table corresponding to samples of an operating curve. The operating curve is typically a substantially straight line defining a volts-hertz relationship. When the speed control system determines a desired operating speed, which defines an operating frequency, the motor drive looks up a voltage corresponding to the frequency. The motor drive then generates a motor voltage based on the voltage and the frequency. In another example, a formula or a function embodying the operating curve characteristics is used by CPU 104 to generate the desired motor voltages.

Rectifier 120 is powered by a power source 40 and includes any rectification circuit well known in the art, e.g. a diode bridge, to convert alternating-current (AC) voltage supplied by power source 40 into direct-current (DC) voltage which it supplies to inverter 130. Inverter 130 receives DC power from rectifier 120 through a conductor 122 and converts the DC power into an AC motor power.

CPU 104 receives inputs through an I/O interface 108 and outputs a control signal over line 128 to inverter 130. In one example, the control signal is provided to a pulse-width-modulated (PWM) module having power switches and control logic which generates the appropriate gating signals for the power switches to convert the DC power supplied by rectifier 120 to the AC motor voltage suitable to drive the motor according to the control signal, provided to the motor via conductors 132, 134. Current drawn by inverter 130 from rectifier 120 is sensed by a current sensor 123 and a current signal is provided by current sensor 123 to CPU 104 by conductor 124. Motor voltage feedback can also be provided, for example through conductor 126 connecting inverter 130 and controller 102. Motor voltages may also be generated with other known or later developed drive topologies programmed in accordance with embodiments of the disclosure.

In another embodiment, the system may be a drinking water system in a feedlot and power source 40 may be a renewable energy source powering motor drive 100. Examples of renewable energy sources include solar energy, wind energy, and hydroelectric energy. Reservoir 18 may be sufficiently large to store enough water to supply the animals in the feedlot when renewable energy is low or nonexistent for a period of time. For example, reservoir 18 may store enough water to supply the animals in the feedlot from dusk to dawn, particularly since during this time animals do not require as much water as they do during daytime. Power source 40 in the present embodiment may comprise voltage or current regulators, step-up or step-down converters, and any devices known in the art for conditioning power incoming from the renewable energy source to match the motor drive input requirements. Furthermore, if the renewal energy source generates variable DC power, e.g. solar energy panels, rectifier 120 may be omitted and power source 40 may be coupled to inverter 130.

In a more general embodiment, the controller comprises control logic operable to generate the control signal. The term "logic" as used herein includes software and/or firmware executing on one or more programmable processors, application-specific integrated circuits, field-programmable gate arrays, digital signal processors, hardwired logic, or combinations thereof. Therefore, in accordance with the embodiments, various logic may be implemented in any appropriate fashion and would remain in accordance with the embodiments herein disclosed. A non-transitory machine-readable medium comprising logic can additionally be considered to be embodied within any tangible form of a computer-readable carrier, such as solid-state memory, magnetic disk, and optical disk containing an appropriate set of computer instructions and data structures that would cause a processor to carry out the techniques described herein. A non-transitory computer-readable medium, or memory, may include random access memory (RAM), read-only memory (ROM), erasable programmable read-only memory (e.g., EPROM, EEPROM, or Flash memory), or any other tangible medium capable of storing information.

In a motor driven by a variable frequency drive, torque may be calculated as follows:

$$T = \frac{\sqrt{3} \times V \times I \times PF}{\omega}$$

T – Torque

V – Voltage

I – Current

PF – Power Factor $\omega$ – rotational speed

The torque also has a proportional relationship to the motor's current and is influenced by the actual operating point as well. As an illustration, the current is also influenced by the speed or rather total load on the shaft. Additionally, the load and magnetization component of the current are to be separated so that the load component can be used to establish the correlation. Accordingly, a desired torque level can be caused by controlling the voltage and current according to the present load.

Figure 3:
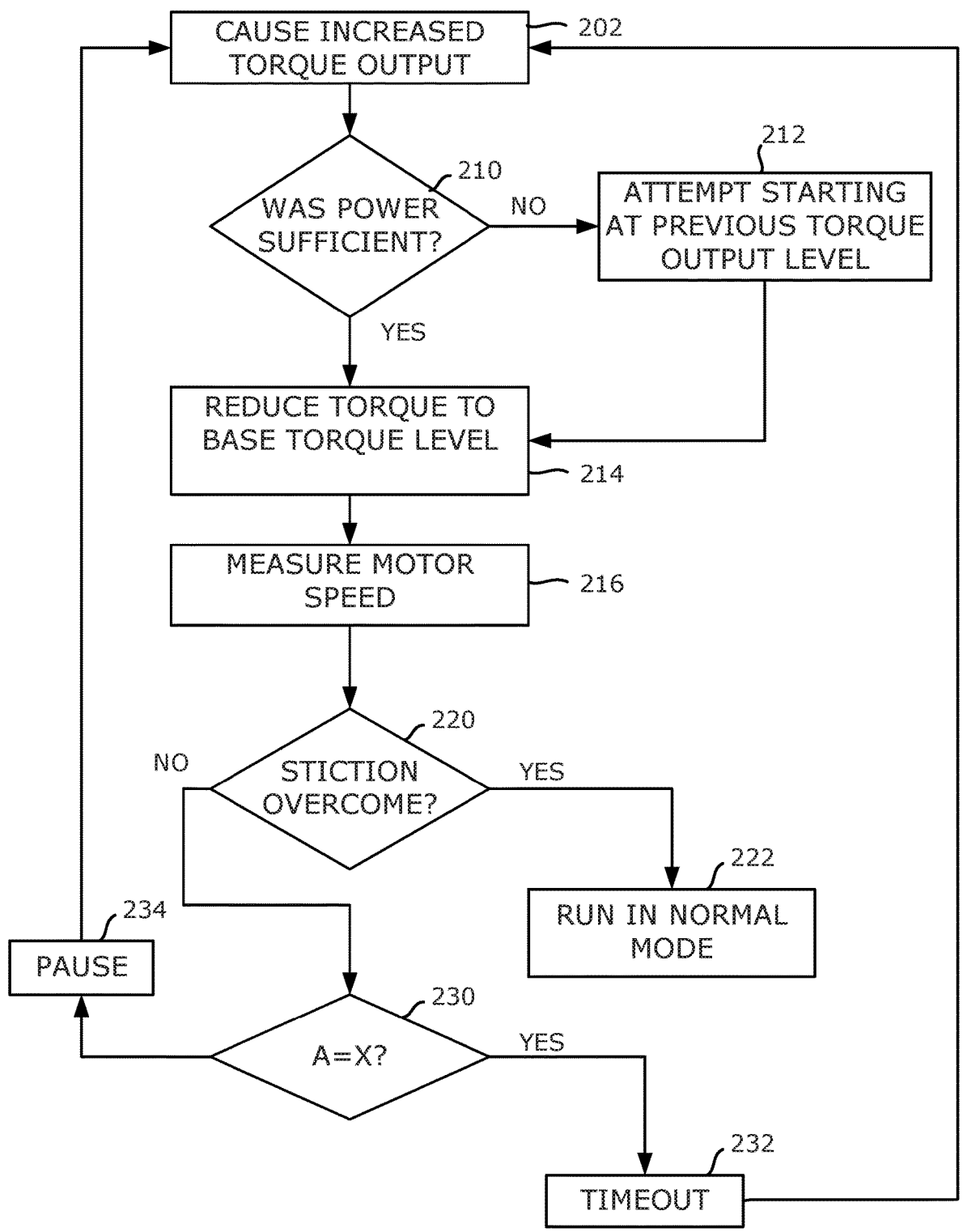
FIG. 3 is a flowchart depicting an embodiment of a method for adaptively controlling a motor driving a helical rotor pump.

Referring now to FIG. 3, a flowchart 200 is provided to depict an embodiment of a method to adaptively control an operating characteristic of a motor in a fluid pumping system. The operating characteristic may be voltage, current, power, or torque, and may be controlled indirectly by controlling one or more of voltage, current, and power. The method can be implemented with a motor drive such as motor drive 100 described with reference to FIG. 2. Timing diagrams illustrating the functionality of the method are described with reference to FIGS. 4 to 6.

Generally, the control logic causes the motor drive to output an amount of power sufficient to cause the motor to generate a first torque level. The motor drive then determines the speed of the motor and if the speed of the motor is consistent with the first torque level, the control logic determines that stiction has been overcome and enters a normal mode of operation. In the normal mode of operation, the motor drive controls the speed of the motor to achieve a desired fluid characteristic. Example fluid characteristics include level, flow, and pressure. Control logic to control the speed of the motor to achieve a desired fluid characteristic are well known.

The speed of the motor is consistent with the first torque level if it falls within a range of speeds that may result from normal operation at the first torque level, when stiction has been overcome. The range of speeds may comprise a narrow band of speeds about a predetermined speed at which the motor would normally operate at the first torque level. The range of speeds represents normal variation in the operation of the system, including speed determination variation. The speed of the motor falls within a range of speeds if it is within the range, which may include the upper and lower range limits. Of course the control logic can be configured to determine that the speed of the motor is consistent with a torque level in any mathematically or electrically equivalent manner. When the speed of the motor is consistent with the corresponding torque level it can be said that the speed of the motor "matches" the corresponding torque level. The lower limit of the range may be considered a "threshold", such that if the motor speed falls below it, the speed is not consistent and does not match a speed corresponding to the torque level.

If the motor speed is not consistent with the first torque level, for example the speed of the motor is lower than a speed corresponding to the first torque level by at least a threshold amount, the control logic determines that stiction has not been overcome. Then, the control logic pauses for a brief moment and then causes the motor drive to output an amount of power sufficient to cause the motor to generate a second torque level for a given time period. The control logic once again measures speed to determine if stiction has been overcome. If the speed of the motor indicates that stiction has not been overcome, the process to overcome stiction is attempted several more times, each time increasing the torque from the second to third, fourth and further torque levels until a predetermined number of starting attempts, denoted by the symbol "X", fail to overcome friction. If that is the case, the control logic enters a timeout mode in which it waits for a prolonged time before repeating the process from the beginning at the first torque level.

When using a constrained power source, the available power may be less than the power required to cause the motor to generate a particular torque level. For example, the motor may not be able to output the fourth torque level. If during the fourth starting attempt the control logic is not able to generate the necessary power, the following starting attempt is performed at the torque level of the preceding starting attempt. If the power collapses at the fourth attempt, then the fifth attempt will be at the power level of the third attempt. In this manner the motor drive will not attempt to start the pump when the requisite amount of power is not available but will continue to attempt to start the drive repeatedly. It has been found that repeated attempts, even at the same torque level, may overcome stiction. It has also been found that the foregoing method iteratively determines the maximum power available from a constrained power source and repeatedly attempts to start the pump at that power level or adjusts the power level if the available power increases or decreases.

A solar power panel is a constrained power source. The solar power panel is constrained by the insolation level. The solar power panel generates maximum power when the voltage is about 78% of the open-circuit voltage of the solar power panel, known as the "knee" of the power curve. Excessive current draw will cause the voltage to collapse, resulting in a collapse of the power output of the solar power panel.

Referring now to FIG. 3, an embodiment of a method for adaptively controlling the torque of a motor is provided. Initially, a first starting attempt comprises the control logic causing the motor drive to output an amount of power sufficient to cause the motor to generate a first torque level. The motor drive then determines the speed of the motor and if the speed of the motor is consistent with the first torque level, the control logic determines that stiction has been overcome and enters the normal mode of operation described above.

If the motor speed is not consistent with the first torque level, for example the speed of the motor is lower than a speed corresponding to the first torque level by at least a threshold amount, the control logic determines that stiction has not been overcome. Then, the control logic pauses for a brief moment and at 202 causes the motor drive to output an amount of power sufficient to cause the motor to generate a second torque level, which may be greater than the first torque level. During the pause, the torque level is reduced below the minimum torque level to keep the pump rotating under normal conditions, which may be zero.

At 210 the control logic determines if sufficient power is available to generate or maintain the increased torque level. The control logic may monitor the voltage and current of the power source to detect a significant decrease in power, indicating a collapse of the power output, or simply the inability of the power source to generate the power needed to reach the desired increased torque level. If not, the control logic pauses and then at 212 attempts starting again at the previous torque output level, in this case the first torque level. If power is sufficient, the second torque level is maintained for a given time period and then, at 214, the torque level is reduced to a base torque level, which may be the minimum torque level to keep the pump rotating after stiction has been overcome.

At 216 the control logic measures the motor speed. In some embodiments, the speed of the motor may be determined without an external or motor mounted speed sensor, and instead may be determined by analyzing current within the motor drive. Algorithms to determine speed based on current, known as "observers," are well known in the art. Accordingly, the motor drive may be said to operate in a sensorless manner. Alternatively, the speed of the motor may be determined by sensing the rotation speed of the rotor of the pump or sensing a mechanically linked device whose speed correlates to the speed of the rotor.

At 220 the control logic compares the speed of the motor to a base speed corresponding to the base torque, and if the speed of the motor is below the base speed by more than a threshold amount, the control logic determines that stiction has not been overcome. If the speed of the motor matches the base speed, the control logic determines that stiction has been overcome.

At 222, if stiction has been overcome the motor drive enters the normal mode of operation. Otherwise at 230 the control logic determines if a predetermined number of starting attempts "X" has been reached, and if so, at 232 the control logic imposes a timeout. If the predetermined number of starting attempts has not yet been reached, then the control logic imposes a pause at 234 and then causes an increased torque output at 202 and again attempts to start the pump.

Figure 4:
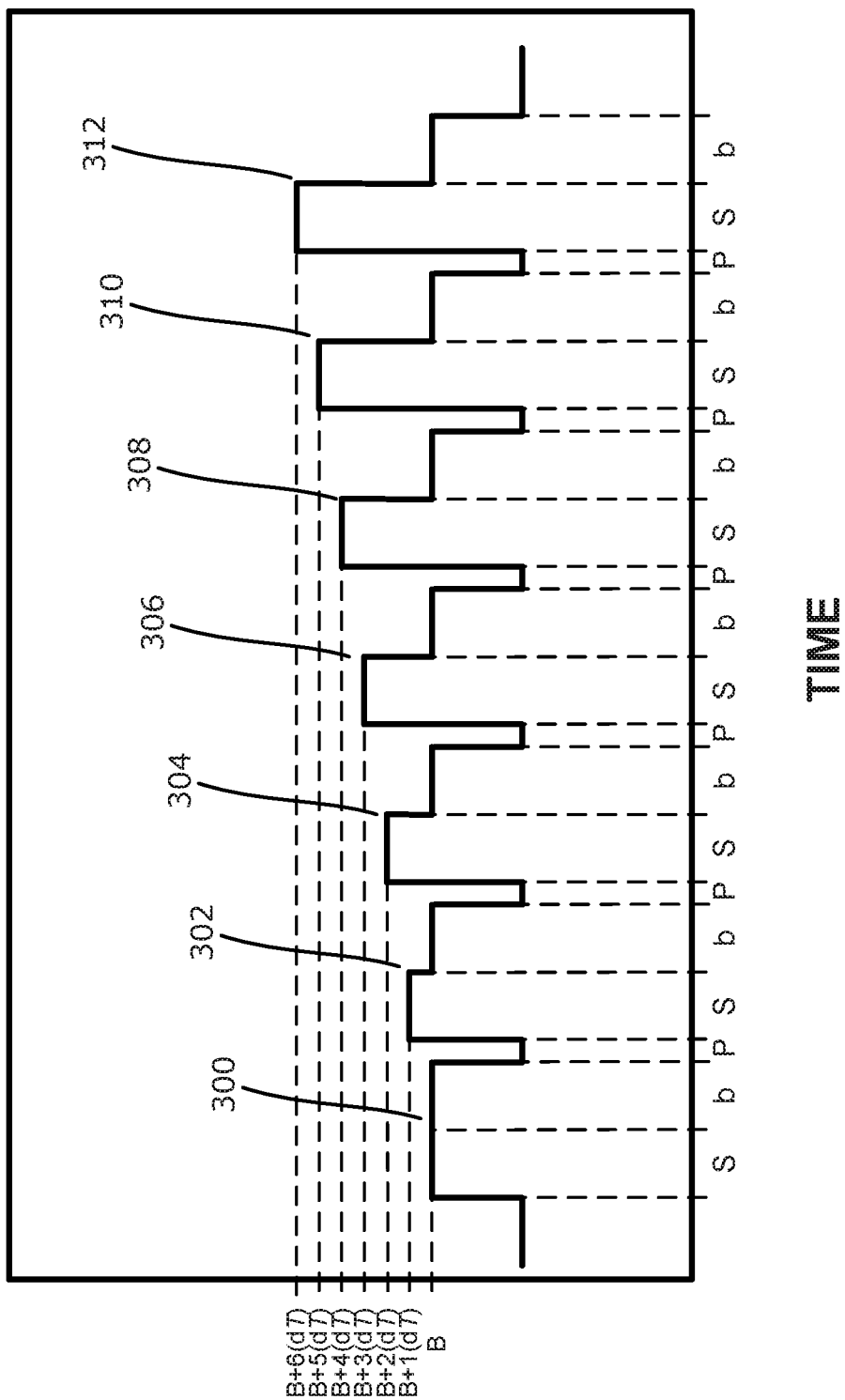

FIG. 4 is a timing diagram illustrating a plurality of consecutive starting attempts 300, 302, 304, 306, 308, 310, and 312 performed in accordance with the method described with reference to FIG. 3. As shown, each starting attempt includes a starting torque level for a period "S" followed by a base torque level for a period "b" followed by a pause "P". The starting torque levels are shown on the vertical axis as B, B+1 (dT), B+2 (dT), B+3 (dT), B+4 (dT), B+5 (dT), and B+6 (dT), where B is a base torque and dT is a torque increment. In the present embodiment, the first starting attempt is performed at the base torque, S and b are each 3 seconds, and P is 1 second. The durations of S, b, and P can be selected by the designer of the control logic based on the capacity of the motor drive and electrical motor, taking account of electrical tolerances, heat dissipation, and other parameters configured to protect the motor drive and motor from damage. In the present embodiment, X=9, meaning that the timeout is imposed after nine failed attempts to overcome stiction. The duration of the timeout is 15 minutes. After the timeout, the control logic retries with attempt 300 again and then continues.

In various other embodiments, the predetermined times during which power is applied at increased and reduced levels varies from one starting attempt to another, and the reduced power level may also vary from one starting attempt to another. For example the subsequent power levels may be higher for a smaller amount of time, thus delivering equal energy with more impact at the risk of collapsing the power source, or reducing the risk of collapse albeit with smaller impact. Further, although the first starting attempt may be performed at the base power level, it may also be performed at a power level higher than the base power level, for example a power level for which "matching" speeds are also defined. Determining whether the motor speed is consistent with the applied torque, when more than a base speed is used for matching, increases the complexity of the control logic but provides additional flexibility to tailor the control logic to specific applications.

FIG. 5 is a timing diagram illustrating a sequence of events, performed in accordance with the method described with reference to FIG. 3, in which stiction was overcome after two starting attempts. Starting attempt 300 was described previously and failed to overcome stiction. Therefore starting attempt 302 is performed, and the control logic determined that friction was overcome. Accordingly, the motor drive entered the normal mode of operation 320 and, for example, increased torque to meet demand.

FIG. 6 is a timing diagram illustrating a sequence of events, also performed in accordance with the method described with reference to FIG. 3, in which stiction was not overcome after three starting attempts, 300, 302, 304, and then power collapsed on the fourth attempt. During the fourth attempt, denoted by numeral 330, power was increased to the fourth torque level but that amount of power was not sustainable during period S. Therefore the power level was reduced for the remainder of period S, period b, and period P, and on a fifth starting attempt 332 power was reduced to generate the preceding, or third, torque level. The amount of power was sustained for the period S and thus the method continued to a sixth starting attempt 334, in which power was increased to generate the next, or fourth, torque level.

The power levels are described herein with reference to increasing and decreasing power levels. The increases and decreases are relative to preceding power levels during corresponding events. Thus an increased power level during a starting event indicates that the increased power level is larger than the power level applied during the preceding starting event and not just relative to a pause or the reduced power level immediately following the power level applied at the beginning of a starting attempt.

Increased and reduced power levels may correspond to desired torque levels. As described previously, torque may be determined based on voltage and current at the present load, therefore target power levels may correspond to target torque levels.

Unless otherwise expressly stated in connection with a specific use thereof, the term "device" includes a single device, a plurality of devices, two components integrated into a device, and any variations thereof. The singular form is only used to illustrate a particular functionality and not to limit the disclosure to a single component. Therefore, a controller includes, for example, a central processing unit, a math processing unit, a plurality of processors on a common integrated circuit, and a plurality of processors operating in concert, whether physically or electronically coupled. Furthermore and in a similar manner, the term "program" includes a single application, a plurality of applications, one or more subroutines, software, firmware, and any variations thereof suitable to execute instruction sequences with a controller.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A method of attempting to start, or starting pumping in a normal mode of operation in a water pumping system, the method comprising:
    performing repeated starting attempts to overcome stiction in a progressive cavity pump by attempting to supply power to an electrical motor driving the progressive cavity pump at increasing power levels in each starting attempt and supplying the power at the increasing power levels if the power is available from a power source; and
    after each starting attempt:
        reducing the power applied to the electrical motor to a reduced power level;
        determining a rotational speed of the electrical motor at the reduced power level;
        determining if the rotational speed matches a speed corresponding to the reduced power level applied to the electrical motor;
        if the rotational speed does not match the speed corresponding to the reduced power level, and a predetermined number of the starting attempts has not been reached, performing a next starting attempt; and
        if the rotational speed does match the speed corresponding to the reduced power level, entering the normal mode of operation.

2. The method of claim 1, wherein during each starting attempt the increased power level is supplied for a first predetermined time before the power is reduced.

3. The method of claim 2, wherein during each starting attempt the reducing the power applied to the electrical motor comprises supplying the power at the reduced power level for a second predetermined time.

4. The method of claim 3, wherein the reduced power level is the same for each starting attempt.

5. The method of claim 4, wherein the reduced power level is configured to generate a base torque, and wherein the increasing power levels are configured to generate a predetermined torque increase between successive starting attempts of the repeated starting attempts.

6. The method of claim 3, wherein the first predetermined time equals the second predetermined time.

7. The method of claim 3, wherein the first predetermined time is the same for each starting attempt.

8. The method of claim 3, wherein the second predetermined time is the same for each starting attempt.

9. The method of claim 3, wherein after the determining the speed of the electrical motor and before performing the next starting attempt the method further comprises pausing the supply of power to the electrical motor for a pause period.

10. The method of claim 9, wherein a sum of the first predetermined time, the second predetermined time, and the pause period is less than 10 seconds.

11. The method of claim 10, wherein the predetermined number of starting attempts is less than 10.

12. The method of claim 10, wherein if the rotational speed does not match the speed corresponding to the reduced power applied to the electrical motor, and the predetermined number of starting attempts has been reached, the method further comprises discontinuing the power supply to the electrical motor for a timeout period.

13. The method of claim 12, wherein the timeout period is greater than 5 minutes.

14. The method of claim 1, wherein if the power is not available from the power source, the method comprises:
    reducing the power applied to the electrical motor; and
    performing a starting attempt at a power level of an immediately preceding starting attempt.

15. The method of claim 1, wherein if the rotational speed does not match the speed corresponding to the reduced power applied to the electrical motor, and the predetermined number of starting attempts has been reached, the method further comprises discontinuing the power supply to the electrical motor for a timeout period.

16. The method of claim 15, wherein the timeout period is greater than 5 minutes.

17. The method of claim 1, wherein the attempting to supply the power to the electrical motor driving the progressive cavity pump comprises drawing the power from the power source, wherein the power source is a constrained power source.

18. The method of claim 17, wherein the constrained power source comprises a solar power panel.

19. An electrical motor drive configured to start a progressive cavity pump in a normal mode of operation in a water pumping system, the electrical motor drive comprising a controller including control logic configured to perform a method comprising:
performing repeated starting attempts to overcome stiction in the progressive cavity pump by attempting to supply power to an electrical motor driving the progressive cavity pump at increasing power levels in each starting attempt and supplying the power at the increasing power levels if the power is available from a power source; and
after each starting attempt:
reducing the power applied to the electrical motor to a reduced power level;
determining a rotational speed of the electrical motor at the reduced power level;
determining if the rotational speed matches a speed corresponding to the reduced power level applied to the electrical motor;
if the rotational speed does not match the speed corresponding to the reduced power level, and a predetermined number of the starting attempts has not been reached, performing a next starting attempt; and
if the rotational speed does match the speed corresponding to the reduced power level, entering the normal mode of operation.

20. A water pumping system comprising:
a progressive cavity pump;
an electrical motor coupled to the progressive cavity pump; and
an electrical motor drive to power the electrical motor, the electrical motor drive configured to start the progressive cavity pump and to drive the progressive cavity pump in a normal mode of operation after starting the progressive cavity pump, the motor drive including a controller comprising control logic configured to perform a method comprising:
performing repeated starting attempts to overcome stiction in a progressive cavity pump by attempting to supply power to an electrical motor driving the progressive cavity pump at increasing power levels in each starting attempt and supplying the power at the increasing power levels if the power is available from a power source; and
after each starting attempt:
reducing the power applied to the electrical motor to a reduced power level;
determining a rotational speed of the electrical motor at the reduced power level;
determining if the rotational speed matches a speed corresponding to the reduced power level applied to the electrical motor;
if the rotational speed does not match the speed corresponding to the reduced power level, and a predetermined number of the starting attempts has not been reached, performing a next starting attempt; and
if the rotational speed does match the speed corresponding to the reduced power level, entering the normal mode of operation.

21. The water pumping system of claim 20, wherein the electrical motor drive further comprises an inverter controlled by the controller to power the electrical motor, and the control logic is further configured to analyze a current drawn by the electrical motor to determine the rotational speed of the electrical motor.

22. The water pumping system of claim 21, further comprising a solar array electrically coupled to the electrical motor drive to supply power to the electrical motor drive.

* * * * *